US011925686B2

(12) United States Patent
Sui et al.

(10) Patent No.: US 11,925,686 B2
(45) Date of Patent: *Mar. 12, 2024

(54) MATERIALS FOR PHOTOTHERAPIES OF OPHTHALMIC DISEASES

(71) Applicant: EYEBRIGHT MEDICAL TECHNOLOGY (BEIJING) CO., LTD., Beijing (CN)

(72) Inventors: Xince Sui, Beijing (CN); Yongji Wei, Beijing (CN); Jiangbing Xie, Beijing (CN)

(73) Assignee: EYEBRIGHT MEDICAL TECHNOLOGY (BEIJING) CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/746,746

(22) PCT Filed: Jul. 22, 2016

(86) PCT No.: PCT/CN2016/090980
§ 371 (c)(1),
(2) Date: Jan. 22, 2018

(87) PCT Pub. No.: WO2017/012578
PCT Pub. Date: Jan. 26, 2017

(65) Prior Publication Data
US 2018/0214552 A1    Aug. 2, 2018

(30) Foreign Application Priority Data
Jul. 23, 2015 (CN) .......................... 201510436196.3

(51) Int. Cl.
*A61K 41/00* (2020.01)
*A61F 9/007* (2006.01)
*A61F 9/008* (2006.01)
*A61K 47/58* (2017.01)
*A61K 47/69* (2017.01)
*A61N 5/06* (2006.01)

(52) U.S. Cl.
CPC ........ *A61K 41/0071* (2013.01); *A61F 9/0079* (2013.01); *A61F 9/008* (2013.01); *A61K 41/0057* (2013.01); *A61K 41/0076* (2013.01); *A61K 47/58* (2017.08); *A61K 47/6957* (2017.08); *A61N 5/062* (2013.01); *A61N 2005/0648* (2013.01)

(58) Field of Classification Search
CPC ............ A61K 41/0071; A61K 41/0057; A61K 41/0076; A61K 47/58; A61K 47/6957; A61F 9/0079; A61F 9/008; A61N 5/062; A61N 2005/0648
See application file for complete search history.

(56) References Cited

U.S. PATENT DOCUMENTS

| 5,756,541 | A    | 5/1998  | Strong et al. |
|-----------|------|---------|---------------|
| 5,770,619 | A    | 6/1998  | Richter et al. |
| 5,798,349 | A    | 8/1998  | Levy et al. |
| 7,909,458 | B2 * | 3/2011  | Schlueter ............. C07D 249/06 351/159.02 |
| 8,450,359 | B2 * | 5/2013  | McCoy ................... A61P 31/12 514/410 |
| 11,318,226 | B2 * | 5/2022 | Sui .......................... A61L 27/16 |
| 2009/0287306 | A1 * | 11/2009 | Smith ................... A61F 2/1627 623/5.16 |
| 2012/0158133 | A1 * | 6/2012 | Mueller-Lierheim ...................... A61F 2/1664 623/6.56 |
| 2012/0184495 | A1 * | 7/2012 | Koyakutty ......... A61K 49/0019 514/19.3 |

FOREIGN PATENT DOCUMENTS

| CN | 1326362 |     | 12/2001 |
|----|---------|-----|---------|
| CN | 1578647 | A   | 2/2005  |
| CN | 1935273 |     | 3/2007  |
| CN | 102065795 | A | 5/2011  |
| CN | 102573910 | A | 7/2012  |
| CN | 102617784 | A | 8/2012  |
| CN | 103083133 | A | 5/2013  |
| CN | 103153396 | A | 6/2013  |
| JP | 2002523509 |   | 7/2002  |
| JP | 2007535540 |   | 12/2007 |
| JP | 2009511456 |   | 3/2009  |
| JP | 2009525108 |   | 7/2009  |

(Continued)

OTHER PUBLICATIONS

Lee et al., J. Chem. Soc. Perkin Trans.,1, pp. 2369-2377. (Year: 1993).*
Maclean M, Macgregor SJ, Anderson JG, Woolsey GA. The role of oxygen in the visible-light inactivation of *Staphylococcus aureus*. J Photochem Photobiol B. Sep. 18, 2008;92(3):180-184. (Year: 2008).*
Valkov, Anton, Faina Nakonechny, and Marina Nisnevitch. "Polymer-immobilized photosensitizers for continuous eradication of bacteria." International journal of molecular sciences 15.9 (2014): 14984-14996. (Year: 2014).*

(Continued)

*Primary Examiner* — Abigail Vanhorn
(74) *Attorney, Agent, or Firm* — Myers Bigel, P.A.

(57) ABSTRACT

The present invention relates to a medicinal material for light therapy, comprising a matrix material and a photosensitizer, wherein the photosensitizer is dispersed inside the matrix material by copolymerization, is mixed inside the matrix material, or attached to the surface of the matrix material by surface grafting, modification, coating and the like. The present material can kill diseased tissue cells with a radiation under selected wavelength so as to obtain a phototherapy treatment of ophthalmic diseases. The present invention also provides a process for preparing the material and a use in preparing an ophthalmic medical device.

7 Claims, No Drawings

(56) References Cited

FOREIGN PATENT DOCUMENTS

| | | |
|---|---|---|
| JP | 2012529500 | 11/2012 |
| JP | 2013513610 | 4/2013 |
| JP | 2014524465 | 9/2014 |
| WO | 97/33619 A1 | 9/1997 |
| WO | 98/25610 A1 | 6/1998 |
| WO | 98/25648 A2 | 6/1998 |
| WO | 00/12512 | 3/2000 |
| WO | 03/061696 | 7/2003 |
| WO | 2005/110365 | 11/2005 |
| WO | 2007/042775 | 4/2007 |
| WO | 2007/088392 | 8/2007 |
| WO | 2009/105209 | 8/2009 |
| WO | 2009/143054 | 11/2009 |
| WO | 2010/143942 | 12/2010 |
| WO | 2011/071970 | 6/2011 |
| WO | 2013/027222 | 2/2013 |
| WO | 2013/027222 A1 | 2/2013 |

OTHER PUBLICATIONS

Office Action corresponding to Chinese Application No. 201510436196.3 dated Mar. 4, 2019.

International Search Report corresponding to International Application No. PCT/CN2016/090980 dated Oct. 17, 2016.

Renno et al. "Selective Photodynamic Therapy by Targeted Verteporfin Delivery to Experimental Choroidal Neovascularization Mediated by a Homing Peptide to Vascular Endothelial Growth Factor Receptor-2", Arch Ophthalmol. 122:1002-1011 (2004).

Extended European Search Report corresponding to European Application No. 16827269.8 dated Jul. 2, 2019.

Peterson et al. "Combination Chemotherapy and Photodynamic Therapy with N-(2-Hydroxypropyl)methacrylamide Copolymer-bound Anticancer Drugs Inhibit Human Ovarian Carcinoma Heterotransplanted in Nude Mice", Cancer Research 56:3980-3985 (1996).

Office Action corresponding to Japanese Application No. 2018-503474 dated Jul. 9, 2019.

Office Action corresponding to Chinese Application No. 201510436196.3 dated Nov. 8, 2019.

Office Action corresponding to Chinese Application No. 201510436196.3 dated Mar. 19, 2020.

Decision of Refusal corresponding to Japanese Application No. dated May 26, 2020.

Office Action corresponding to Chinese Application No. 201510436196.3 dated Sep. 14, 2020.

Third Office Action issued in corresponding Chinese Patent Application No. 201510436196.3, dated Jan. 28, 2021 (including English translation).

* cited by examiner

MATERIALS FOR PHOTOTHERAPIES OF OPHTHALMIC DISEASES

RELATED APPLICATIONS

This application is a 35 U.S.C. § 371 national phase application of and claims priority to PCT Application PCT/CN2016/090980 filed Jul. 22, 2016, which claims priority to Chinese Application No, 2015104361963 filed Jul. 23, 2015, the entire contents of each of which is incorporated herein by reference in, their entirety.

TECHNICAL FIELD

The present invention relates to a medical material for phototherapy, particularly, an ophthalmic material for phototherapy of ophthalmic diseases and also relates to a process for preparing them.

BACKGROUND OF TECHNOLOGY

Various types of ocular diseases such as eyelid disease, lacrimal disease, conjunctival diseases, corneal diseases, scleropathy, uveal diseases, cataracts, second cataract, glaucoma, vitreous lesions, lens diseases, iris disorders, retinal diseases, macular degeneration, optic tract disease, orbital disease, eye injury, eye refraction, eye myopathies, ocular tumors, etc., especially some intra-ocular diseases, can lead to patients with blurred vision or even blindness, which results in a huge inconvenience and pain of patients. Due to a unique physiological structure of the human eye, many diseases can only be treated by surgery. In view of the fact that the structure of the human eye is very complicated and the intraocular tissue is very fine and small, the operation is very difficult. Sometimes the second operation is needed, which also gives patients with great inconvenience and high expense.

The laser-driven phototherapy has achieved remarkable results in a treatment of a cancer. The laser-driven phototherapy has many advantages, for example, non-invasiveness, non-toxicity and high efficiency. It has been drawn more and more attention in ophthalmology in recent years. The light therapy cited in prior art uses the near-infrared light that penetrates the skin to activate nano-material and obtains a photodynamic effect or a photothermal effect, which acts on the tumor site to achieve the purpose of killing the tumor cells. Depending on the mechanism of action of laser-irradiated materials, the treatments can be divided into a photodynamic therapy and a photothermal therapy.

The photodynamic therapy, also known as photochemotherapy, is based on the interaction of light, photosensitizers and oxygen, wherein the photosensitizers is used to absorb photons so as to be in the excited state, and then the energy is passed to the surrounding oxygen so as to result in a singlet-oxygen with a strong activity; the singlet oxygen, on the one hand, can cause an acute microvascular injury in diseased tissues, cause vascular blockages and cause ischemia, on the other hand, the singlet oxygen can directly kill diseased tissue cells, so as to achieve the purpose of local treatment.

The photothermal therapy, also known as a photophysical treatment, is similar to the photodynamic therapy. The photothermal therapy is also a laser medical technique for the treatment of localized lesions in humans. The photothermal therapy is based on photothermal transfers, wherein the photothermal agents efficiently convert light energy into heat and produce a high temperature to kill diseased tissue cells under a radiation of laser with the selected wavelengths. When the temperature of the diseased tissue region reaches 43° C., such condition can inhibit DNA, RNA and protein synthesis. The safety limit of a normal cell is 45° C.

Both of the photothermal therapy and the photodynamic therapy are ideal treatments. Both of them have a local lethality for lesion tissues and are noninvasive treatments by laser.

In recent years, the photodynamic therapy or the photothermal therapy in the field of ophthalmology research has also been drawn attention. WO2013/027222 discloses a chlorophyll photosensitizer for the treatment of eye diseases; CN103083133 discloses a laser photothermal therapy system for treating an ophthalmological disease includes a rod of nano-gold. WO97/33619 discloses a process for improving eyesight by a photodynamic therapy of eyes. WO 98/25648 discloses a photosensitizer compound for preparing drugs of a photodynamic therapy for ocular diseases. WO 98/25610 discloses a green porphyrin photosensitizer for the treatment of second cataract.

However, the conventional photodynamic therapy and the conventional photothermal therapy are limited because of photosensitizers such that they cannot be widely used. The photosensitizers used for the conventional photodynamic therapy and the conventional photothermal therapy include photodynamic-type photosensitizers and photothermal-type photosensitizers, which are needed to be made into liquid pharmaceuticals, and enter into blood and then enter into the diseased tissue by intravenous injection, or directly are injected into the diseased tissues. After the treatment, the photosensitizer needs to be excreted by degradation or metabolism etc. The traditional photodynamic therapy and the traditional photothermal therapy are greatly limited due to the safety of photosensitizers and its metabolism etc. Although the toxic side effect of the photodynamic therapy is low, the photosensitizer used finally enters into human body and has certain toxicities, and the compounds that react with the photosensitizer have certain toxicities. The photosensitizers generally cannot be used alone, and need to work with other drugs or compounds, which enter into human body as a solution, a suspension or an emulsion. The compounds that react with the photosensitizer also have certain toxicities, and increase a risk of the treatment. In addition, because the photosensitizer needs to be intravenously injected into the body and with a high injection speed and with a high removal speed, the patient's heart and blood vessels and other organs need to withstand the comfortlessness caused by rapid injection of the photosensitizer during the treatment. Moreover, only when the photosensitizer goes through the diseased tissue, the laser radiation can be carried out and make an effective treatment. Therefore, the timing and maintenance of administration are difficult to control so that the treatment is difficult.

CONTENT OF INVENTION

The present invention provides a medical material for the photodynamic therapy and the photothermal therapy that can overcome the drawbacks of the conventional photodynamic therapy and photothermal therapy. The present invention also provides its preparation process and the use thereof.

The present invention provides a medical material for phototherapy (including the photodynamic therapy and the photothermal therapy), and in particular, an ophthalmic material for treatments of ocular diseases, comprising: a matrix material and at least one photosensitizer, wherein the photosensitizer is dispersed inside the matrix material by copolymerization, mixing or the like, or attached to the surface of the matrix material by surface graft, modification, coating and the like so as to form the medical materials of the present invention, particularly, a medical material for a treatment of ocular diseases.

The materials of the present invention combine a photosensitizer with a matrix material so that the photosensitizer is fixed inside or at the surface of the matrix material and is surgically implanted into the diseased region. When the diseased region needs to be treated, the diseased region is radiated by a laser beam with the selected wavelength. When the treatment is finished, the only thing is to remove the laser. Since the photosensitizer is fixed inside of the material or is bound to the surface of the material, the photosensitizer cannot freely enter into other tissues in the body via the blood or other body fluids. Therefore, the toxicity of the photosensitizer can be neglected; and the selection of the photosensitizer is no longer limited. In particular, the materials provided by the present invention may be pre-implanted into a potentially diseased tissue or region (site) via others surgery (such as an ophthalmologic operation). On the one hand, the above operation plays a preventive role; on the other hand, once the tissue or region (site) has a disease, it is possible to make a laser treatment without further an additional surgery. More particularly, the material provided by the present invention has repetitive effects. When one laser treatment is completed, the photosensitizer still exists in the diseased region because the photosensitizer is not eliminated, and when a disease occurs for more than one time in said diseased region, a laser treatment can be made without repeatedly injecting the photosensitizer.

Particularly, the present invention relates to a medical material for light therapy method. In particular, the present invention relates to an ophthalmic material for phototherapy of ophthalmic diseases, comprising:
  a matrix material;
  at least one photosensitizer selected from photodynamic type photosensitizers and/or photothermal type photosensitizers;
  in which, the photosensitizer and the matrix material are combined by the following manners selected from:
    participating a polymerization of the matrix material with the photosensitizers during molding the matrix material;
    adding the photosensitizer into the matrix material by a physical dispersion during molding the matrix material;
    fixing the photosensitizer by surface graft or surface-modification on the surface of the formed matrix material; and/or
    fixing the photosensitizer by surface-coating on a surface of the formed matrix material.

When (1) the photosensitizer and the matrix material are combined by participating a polymerization of the matrix material with the photosensitizers during molding the matrix material, the matrix material is a material comprising a polymerizable monomer.

When (2) the photosensitizer and the matrix material are combined by adding the photosensitizer into the matrix material by a physical dispersion during molding the matrix material, the matrix material may be any suitable materials, optionally including a polymerizable monomer.

When (3) the photosensitizer and the matrix material are combined by fixing the photosensitizer by surface graft or surface-modification on the surface of the formed matrix material, the matrix material is a formed matrix material, and the material comprises a polymerizable group on the surface of the formed matrix material. The polymerizable group is, for example, vinyl, allyl, butenyl, acryloxy, methacryloxy, acrylamide, methacrylamide, vinyl ether group, alkynyl, hydroxy, mercapto group, amino, imino, carboxyl group, acid anhydride group, aldehyde group, isocyanate group, siloxane group, epoxy group, azacyclo group, and the like.

When (4) the photosensitizer and the matrix material are combined by fixing the photosensitizer by surface-coating on a surface of the formed matrix material, the matrix material is a formed material which may be any materials that can be coated with a photosensitizer.

In another embodiment of the present invention, the photosensitizer can comprise a polymerizable group in its molecular structure, such as vinyl, allyl, butenyl, acryloxy, methacryloxy, acrylamide, methacrylamide, vinyl ether group, alkynyl, hydroxy, mercapto group, amino, imino, carboxyl group, acid anhydride group, aldehyde group, isocyanate group, siloxane group, epoxy group, azacyclo group, and the like.

In one embodiment of the present invention, the photosensitizer is selected from the group consisting of: indocyanine monocyanine (monomethine cyanine), indocarbocyanine (trimethine cyanine), indodicarbocyanine (pentamethine cyanine), indotricarbocyanine (heptamethine cyanine), tricarbocyanine dyes, benzoindole hemicyanine dyes, indole squarylium cyanine dyes, chlorophyll derivatives, pheophytin, pheophorbide a and its derivatives, chlorine $e_6$ and its derivatives, purpurin 18, chlorine p6 and its derivatives, chlorine f and its derivatives, protoporphyrin and its derivatives, hematoporphyrin derivatives (HpD), porfimer sodium, photocarcinorin (PSD-007), nano-gold, nano-tungsten oxide, nano-copper sulfide, nano-iron oxide, nano-nickel carbide, nano-molybdenum oxide, and its water soluble or liposoluble derivatives with modified based on the above photosensitizer.

In another embodiment of the present invention, the photosensitizer is preferably selected from the group consisting of nano-gold, purpurin 18, fluorescein O-acrylate and fluorescein O-methacrylate and its water soluble or liposoluble derivatives with modified based on the above photosensitizer.

The concentration (or mass fraction) of the photosensitizer in the matrix material can be reasonably controlled such that the actived oxygen or thermal energy with a high-temperature generated under a laser radiation having the selected wavelength can effectively kill the cells in the diseased region while preserving normal cells from loss; at the same time, it is also necessary to minimize a negative impact of photosensitizers on a performance of other raw materials. For example, the amount of the photosensitizer is less than 1%, preferably less than 0.5%, more preferably less than 0.1% relative to the total weight of the material.

In another embodiment of the present invention, the matrix material is selected from the group consisting of hydrophobic acrylates, acrylate hydrogels, silica gels, silicone hydrogels, fluorosilicone acrylate, polystyrene and polymethylmethacrylate, polycarbonates, polysiloxanes, or mixtures thereof.

The present invention also relates to a process for preparing the medical material according to the present invention, comprising the following steps:
  1) mixing a polymerizable monomer with optional additives such as a crosslinking agent, a thermal initiator and/or a UV absorber;
  2) adding a photosensitizer, dissolving it, and then polymerizing.

The present invention also relates to another process for preparing the medical material according to the present invention, comprising the following steps:
1) mixing a polymerizable monomer with optional additives such as a crosslinking agent, a thermal initiator, an ultraviolet absorber and the like, and then polymerizing to obtain a matrix material;
2) adding a photosensitizer that is optionally dissolved with an additive such as a polymerizable monomer, then polymerizing such as a graft polymerization or a surface modification.

The present invention also relates to another process for preparing the medical material according to the present invention, comprising the following steps:
1) mixing a matrix material with a photosensitizer, as well as optional additives such as a masterbatch, stabilizers and the like;
2) molding a mixed raw materials, such as by extrusion, injection molding, blow molding, foaming, calendering, or spinning etc.

The present invention also relates to a medical device comprising the aforementioned medical material of the present invention.

In one embodiment of the present invention, a medical device, in particular an ophthalmic medical device, is preferably selected from the group consisting of: implants such as intraocular lenses for preventing and/or treating a second cataract, corneal contact lens, othokeratology, iris hooks, internal oculoscope, artificial cornea, intracorneal ring, capsular tension ring, intracorneal lens, glaucoma drainage valve, drug sustained-release carrier, intraocular fillers, external medical devices for an external application in contact with body tissues such as skin medical devices, eyeglasses, protective goggles, medical equipment lenses, a telescope, an inspection mirror and fundus fillers.

The present invention also relates to a use of the medical materials of the present invention in preparing a medical device, such as an ophthalmic device.

The present invention also relates to a process for treating related diseases by using a medical device comprising the material according to the present invention, in which the related diseases can be any suitable diseases that can be treated by light therapy (including the photodynamic therapy and the photothermal therapy), for example, cancer, ophthalmology diseases, skin diseases, cardiovascular diseases etc.

DETAILED DISCLOSURE OF THE PRESENT INVENTION

The matrix material of the present invention is selected from a matrix material comprising a polymerizable monomer or any suitable matrix materials preferably having a good biocompatibility. In which, the polymerizable monomer is selected from a hydrophilic polymerizable monomer or a hydrophobic polymerizable monomer.

In one embodiment of the present invention, the matrix material may be a homopolymer of a polymerizable monomer or a copolymer of a plurality of monomers.

In one embodiment of the present invention, the matrix material is a soft material, for example, selected from polymeric materials having a glass transition temperature of less than 20° C., such as polyacrylates, silica gels, polyurethanes, or hydrogels, or foamed materials.

In one embodiment of the present invention, when the material of the present invention is obtained by polymerizing a photosensitizer with a matrix material, the matrix material is selected from the group consisting of a polymerizable matrix material, preferably a polymerizable monomer having a good biocompatibility.

In another embodiment of the present invention, when the material of the present invention is obtained by dispersing a photosensitizer in a matrix material, the matrix material preferably comprises a matrix material having a good biocompatibility, optionally is a polymerizable matrix material.

In another embodiment of the present invention, when a photosensitizer is fixed by surface-grafting or surface-modifying on the surface of the matrix material, the matrix material or the photosensitizer comprises a polymerizable group such as vinyl, allyl, butenyl, acryloxy, methacryloxy, acrylamide, methacrylamide, vinyl ether group, alkynyl, hydroxy, mercapto group, amino, imino, carboxyl group, acid anhydride group, aldehyde group, isocyanate group, siloxane group, epoxy group, azacyclo group, and the like, wherein the matrix material is preferably a matrix material having a good biocompatibility.

In another embodiment of the present invention, when a photosensitizer is fixing on the surface of the matrix material by surface-coating, the matrix material is selected from any suitable matrix materials having a good biocompatibility.

In another embodiment of the present invention, the matrix material may be, but is not limited to, silicon hydrogel, fluorosilicone acrylate, silicone, polystyrene, methyl methacrylate, siloxane, methylsiloxane, phenylsiloxane, vinylsiloxane, acrylate-based siloxane, methacrylate-based siloxane, or mixtures of the above.

In another embodiment of the present invention, the matrix material according to the present invention may also be a polymer selected from the group consisting of: polyacrylates, polymethacrylates, polyacrylamides, polymethacrylamides, polyacrylic acids, polymethacrylic acid, polyhydroxyacrylate, polyhydroxymethacrylate, polystyrene, polyethylene, polypropylene, polyvinyl ether, polyvinyl alcohol, polyvinyl acetate, polyethylene glycol, polypropylene glycol, polyvinylpyrrolidone, polysiloxanes, polyurethane, polyetheretherketone, polycarbonate, polyamide (nylon), polyethylene terephthalate, polybutylene terephthalate, polyformaldehyde, polyvinyl chloride, ABS, polysulfone polytetrafluoroethylene, polysaccharides, collagen, natural polymers and the like, derivatives of the above polymers, copolymers of the above polymers, or mixtures thereof.

In another embodiment of the present invention, the matrix material may also be a hydrogel, including but not limited to collagen, gelatin, keratin, elastin, vegetable protein, reticulin and quaternized protein, etc. or polysaccharides, heparin, chondroitin sulfate, hyaluronic acid, acacia, agar, carrageenan, pectin, guar gum and alginates and the like, or modified starches, modified celluloses, carboxymethyl starch, starch acetate, methylcellulose, ethylcellulose, hydroxymethylcellulose, hydroxyethylcellulose, hydroxypropylcellulose, carboxymethylcellulose and the like, or polyvinyl acetate, polymethylvinyl ether, polyvinyl alcohol, polyethylene glycol, polyoxyethylene, polyacrylamide (PAM), hydrolyzed polyacrylamide (HPAM), polyvinylpyrrolidone (PVP), polyethyleneimine (PEI), or blends thereof.

Preferably, the polymerizable monomer contained in the matrix material is selected from the group consisting of: methyl methacrylate, ethyl methacrylate, ethyl acrylate, butyl methacrylate, butyl acrylate, trifluoroethyl methacrylate, trifluoroethyl acrylate, hydroxyethyl methacrylate, hydroxyethyl acrylate, vinyl pyrrolidone, phenyl ethyl methacrylate, phenylethyl acrylate, phenoxyethyl methacrylate, phenoxyethyl acrylate, benzyl methacrylate, benzyl acrylate, ethoxyethoxyethyl methacrylate, ethoxyethoxyethyl acrylate, ethoxyethyl methacrylate, ethoxyethyl acrylate, ethylene glycol dimethacrylate, butylene glycol dimethacrylate, hexanediol dimethacrylate, styrene, methylstyrene, divinylbenzene, hydroxymethylcellulose, sodium hyaluronate, collagen, and silanes and siloxanes, including, for example, methyltrichlorosilane, dimethyldichlorosilane, methyltriethoxysilane, methyltrimethoxysilane, phenyltrimethoxysilane, (3,3,3-trifluoropropyl) methyldimethoxy silane, vinyltriethoxysilane or vinyltrimethoxysilane, methacryloyloxypropyltris (trimethylsiloxy) silane, 3-(methacryloyloxy) propyltrimethoxy silane, block copolymers of dimethylsiloxane and diphenylsiloxane, diethylene-terminated vinyl silicone oils, 3-(methacryloyloxy) propyltrimethoxysilane, allyltriethoxy silane, allyltris (trimethylsiloxy) silane, 3-acryloxypropyltrimethoxysilane, hexamethylcyclotrisiloxane, octamethylcyclotetrasiloxane, mixed cyclosiloxane, trifluoropropylmethylcyclotrisiloxane or tetrafluorobutylmethylcyclotetrasiloxane, or a mixture thereof.

Other polymerizable monomers used in the present invention include: butadiene, styrene, α-methyl styrene, sodium styrene sulfonate, vinyl toluene, acrylonitrile, methacrylonitrile, α-chloropropylene nitrile, ethacrylonitrile, methyl vinyl ether, isopropyl vinyl ether, n-butyl vinyl ether, isobutyl vinyl ether, t-butyl vinyl ether, 2-ethylhexyl vinyl ether, 4-hydroxybutyl vinyl ether, 1, 4-butanediol divinyl ether, diethylene glycol divinyl ether, vinyl esters such as vinyl acetate, vinyl esters of alkyl hydroxycarboxylic acid, vinyl propionate esters, vinyl butyrate, vinyl isobutyrate, vinyl hexanoate, vinyl 2-ethylhexanoate and vinyl caprate; allyl chloride, methallyl chloride, dichloroethylene, vinyl chloride, vinyl fluoride, vinylidene fluoride, sodium vinyl sulfonate, butyl vinyl sulfonate, phenyl vinyl sulfone, methyl vinyl sulfone, N-vinyl pyrrolidinone, N-vinyloxazolidinedione, acrolein, acrylamide, methacrylamide, N, N-dimethyl (meth) acrylamide, methylol acrylamide, N-butoxy (meth) acrylamide, isobutoxy (meth) acrylamide and the like; and other ethylenically unsaturated carboxylic acids and esters thereof such as dialkyl ester of di- and tri-carboxylic acids (such as itaconic acid and the like) and trialkyl esters of di- and tri-carboxylic acids, including di (2-ethylhexyl) maleate, dibutyl maleate, dimethyl fumarate, dimethyl itaconate, diethyl citraconate, trimethyl aconitate, diethyl mesaconate, di (2-ethylhexyl) itaconate, (2-chloroethyl) itaconate, maleic acid, maleic anhydride, fumaric acid, itaconic acid; and olefins such as diisobutylene, 1-octene, 1-decene, 1-hexadecene, or a mixture thereof.

In another embodiment of the present invention, the polymerizable monomer contained in a matrix material is selected from the group consisting of siloxanes, methylsiloxanes, phenylsiloxanes, vinylsiloxanes, acrylate-based siloxanes, methylacrylate-based siloxanes, or a mixture of the foregoing.

The photosensitizer of the present invention is selected from a photodynamic type photosensitizer or a photothermal type photosensitizer. In another embodiment of the present invention, the photosensitizers of the present invention are any photosensitizer that can be activated by a laser light source in the wavelength range of 300 to 1100 nanometers. Preferably, the wavelength range of a laser light source is selected from 500 to 1000 nm; preferably, the wavelength range of a laser light source is selected from 600 to 900 nm; preferably, the wavelength range of a laser light source is selected from 700 to 900 nm or the wavelength range of a laser light source is selected from 800 to 1100 nm.

In one embodiment of the present invention, the material containing a photodynamic photosensitizer of the present invention is radiated with a laser light with a selected wavelength (for example, 300~1100 nanometers), wherein the photosensitizer in the material is excited so as to generate cytotoxic activated oxygens, which can kill diseased cells and achieve effective effects of treatment.

In another embodiment of the present invention, the material containing a photothermal type photosensitizer is radiated with a laser light with a selected wavelength (for example, 300~1100 nanometers), wherein the photosensitizer in the material is excited, and the optical energy is converted into heat energy so as to raise the ambient temperature to enough high to kill diseased tissue cells. DNAs, RNAs and protein synthesis can be inhibited when the temperature in the diseased tissue region reaches 43° C. The safety temperature of normal cells is 45° C. Therefore, in a preferred embodiment, the material containing a photothermal type photosensitizer is capable of generating heat under a laser radiation so that the temperature is raised 4~20° C.; in a more preferred embodiment, the material containing a photothermal type photosensitizer is capable of generating heat under laser radiation so that the temperature is raised 6~12° C.; in a more preferred embodiment, the material containing a photothermal type photosensitizer is capable of generating heat under a laser irradiation so that the temperature is raised 8 to 10° C., such as elevating the temperature to be greater than 38° C., greater than 39° C., preferably greater than 40° C., preferably greater than 41° C., preferably greater than 42° C., preferably greater than 43° C., preferably greater than 44° C., preferably greater than 45° C., preferably greater than 46° C., preferably greater than 47° C., preferably greater than 50° C., and greater than 550° C., preferably greater than 56° C., preferably greater than 57° C., preferably greater than 58° C., preferably greater than 59° C., preferably greater than 60° C., preferably greater than 61° C., preferably greater than 62° C., preferably greater than 63° C., preferably greater than 64° C., preferably greater than 65° C., and preferably less than 66° C., preferably less than 65° C., preferably less than 64° C., preferably less than 63° C., preferably less than 62° C., preferably less than 61° C., preferably less than 60° C., preferably less than 59° C., preferably less than 58° C., preferably less than 57° C., preferably less than 56° C., preferably less than 55° C., preferably less than 54° C., preferably less than 53° C., preferably less than 52° C., preferably less than 51° C., preferably less than 50° C., preferably less than 49° C., preferably less than 48° C., preferably less than 47° C., preferably less than 46° C.

The photosensitizers suitable for the present invention are selected from the group consisting of: porphyrins, metalloporphyrins, porphins, chlorophyll, purpurin, fluorescein, phthalocyanine, metallophthalocyanine, indocyanine green, tricarbocyanine, nano-gold particulate, metal oxide nanoparticles, metal sulfide nanoparticles, metal carbide nanoparticles, carbon nanotubes, graphene, etc., and derivatives of the above compounds, or degraded products of the above compounds, or salts of the above compounds. In a preferred embodiment, the photosensitizer is selected from the group consisting of: indocyanine monocyanine (monomethine cyanine), indocarbocyanine (trimethine cyanine), indodicarbocyanine (pentamethine cyanine), indotricarbocyanine (heptamethine cyanine), tricarbocyanine dyes, benzoindole hemicyanine dyes, indole squarylium cyanine dyes, phtalocyanine, chlorophyll derivatives, pheophytin, pheophorbide a and derivatives thereof, chlorine $e_6$ and its derivatives, purpurin 18, chlorine p6 and its derivatives, chlorine $e_4$ and its derivatives, chlorine f and its derivatives, protoporphyrin and its derivatives, benzochloroporphyrin, metalloporphyrins, hematoporphyrin derivatives (HpD), porfimer sodium, photocarcinorin (PSD-007), nano-gold, nano-tungsten oxide, nano-copper sulfide, nano-iron oxide, nano-nickel carbide, nano-molybdenum oxide, and its water soluble or liposoluble derivatives with modified based on the above photosensitizer.

In another embodiment of the present invention, the photosensitizer is the photosensitizer that can be activated by a laser light source with a wavelength range of 400~600 nm, such as fluorescein; the photosensitizer is the photosensitizer that can be activated by a laser light source with a wavelength range of 600~750 nm, such as purpurin 18; the photosensitizer is the photosensitizer that can be activated by a laser light source with a wavelength range of 700~900 nm, such as indocyanine green ICG; the photosensitizeris the photosensitizer that can be activated by a laser light source with a wavelength range of 800~1100 nm, such as nano-gold.

In another embodiment of the present invention, the photosensitizer contains a polymerizable group such as vinyl, allyl, butenyl, acryloxy, methacryloxy, acrylamide, methacrylamide, vinyl ether group, alkynyl and the like, which can copolymerize with the monomer of the matrix material. The photosensitizer molecules present in the molecular chain of the matrix material and combine the molecular chain of the matrix material by covalent bonds. Since the photosensitizer is fixed in the matrix material and cannot freely enter the blood or other body fluids, the toxicity of the photosensitizer itself can be completely neglected.

In another embodiment of the present invention, the photosensitizer contains active groups in its molecular structure, for example, hydroxy, mercapto group, amino, imino, carboxyl group, acid anhydride group, aldehyde group, isocyanate group, siloxane group, epoxy group, azacyclo group, and the like, which can be grafted with the groups on the side chains of the matrix material. The photosensitizer molecules covalently bond with the molecular chains of the matrix material, and the photosensitizer is fixed inside or on the surface of the matrix material. They also cannot freely enter into the blood or other body fluids.

In another embodiment of the present invention, the photosensitizer is dispersed in the matrix material by blending or mixing, and the photosensitizer molecules are bound to the molecular chain of the matrix material by hydrogen bond or Van der Waals forces action. The photosensitizer molecules are bound in the matrix material, and cannot freely enter the blood or other body fluids.

In another embodiment of the present invention, the photosensitizer is dispersed in other auxiliary agents (for example, co-solvents, emulsifiers, lubricants, hydrophilic coatings, drug carriers, masterbatchs, ultraviolet absorbers, crosslinking agents, coupling agents, pH adjusting agents, an antistatic agents, releasing agents, etc.) by dissolving, suspending, emulsifying etc. The photosensitizer is coated on the surface of a substrate. The photosensitizer molecules are bound to the molecular chain of the matrix material by hydrogen bond or Van der Waals forces action, in which the photosensitizer is fixed to the surface of the matrix material and cannot freely enter the blood or other bodily fluids.

In another embodiment of the present invention, in order to enhance the affinity between the photosensitizer molecules and the matrix material molecules, the photosensitizer molecules can be chemically modified without changing its photoactivity; the matrix material can also be activated, including but not limited to, plasma treatment, corona treatment, flame treatment, strong acid treatment, strong alkali treatment and the like.

In one embodiment of the present invention, when the photosensitizer is polymerized with the matrix material so as to obtain the material of the present invention, or when the photosensitizer is mixed in the matrix material so as to obtain the material of the present invention, the material of the present invention can be prepared by a process comprising the following steps:
1) mixing a polymerizable monomer with optional additives (such as a crosslinking agent, a thermal initiator and/or a UV absorber etc.);
2) adding a photosensitizer, dissolving it, and then polymerizing.

More particularly, the material of the present invention can be prepared by a process comprising the following steps:
1) mixing an initiator, a cross-linking agent, UV absorber and polymerizable monomer;
2) adding a photosensitizer, dissolving it;
3) adding the above reaction system obtained in step 2) into a mold; and
4) polymerizing, such as polymerizing with water bath.

More particularly, the material of the present invention can be prepared by a process comprising the following steps:
1) mixing the matrix material with the photosensitizer, as well as optional additives such as a masterbatch, stabilizers and the like;
2) molding the mixed raw materials, for example, by extrusion, injection molding, blow molding, foaming, calendering, or spinning etc.

In another embodiment of the present invention, when the photosensitizer is fixed on the surface of the matrix material by surface grafting or surface-modifying, the material of the present invention can be prepared by a process comprising the following steps:
1) mixing a polymerizable monomer with optional additives such as a crosslinking agent, a thermal initiator and/or an ultraviolet absorber;
2) adding a photosensitizer, dissolving it, for example, dissolving the photosensitizer with a suitable adjuvant (such as a polymerizable monomer), and then polymerizing, such as via a graft polymerization or a surface modification or a transfer printing.

More specifically, the material of the present invention can be prepared by a process comprising the following steps:
1) mixing an initiator, a cross-linking agent, UV absorber and polymerizable monomer(s);
2) transferring the above reaction system obtained in step 1) into a mold;
3) polymerizing, such as polymerizing with water bath;
4) re-polymerizing within the dryer;
5) adding the photosensitizer, dissolving, for example, with a suitable adjuvant (such as a polymerizable monomer); and
6) re-polymerizing the system obtained as above.

In another embodiment of the present invention, when the photosensitizer is fixed by surface-coating on the surface of the matrix material, the material of the present invention can be prepared by a process the following steps:
1) providing a suitable matrix material;
2) dissolving the photosensitizer, for example, with a suitable adjuvant (such as a polymerizable monomer), coating it on the surface of the matrix material.

In the process of the present invention, the amount of a cross-linking agent used can be from 0.1 to 20% by weight, relative to the polymerizable monomer(s), preferably from 0.5 to 15%, in particular from 1 to 5%. The amount of an UV absorber is 0-10 wt %, relative to the polymerizable monomer(s), preferably 0-5%, especially 0-1%. The amount of an initiator is 0.01 to 10% by weight, preferably 0.01 to 5%, in particular 0.05% to 1.0%, relative to the polymerizable monomer(s).

In addition to the matrix material and the photosensitizer, the materials of the present invention can include other optional components including but not limited to, co-solvents, pigments, fillers, dispersants, curing agents, wetting agents, defoamers, UV absorbers, antioxidants, sterilizers, stabilizers, emulsifiers, hydrophilic coatings, drug carriers, masterbatch, crosslinking agents, coupling agents, pH adjusting agents, antistatic agents, mold-release agents, and the like.

In the present invention, the material of the present invention may be coated on a desired matrix by using conventional coating techniques such as conventional or airless spraying, roll coating, brushing, curtain coating, shower coating and dip coating. At the same time, the materials of the present invention may be coated on the desired matrix by conventional printing techniques such as conventional relief printing, intaglio printing, lithographic printing, screen printing, thermal transfer printing, xerography, ink jet printing or 3D printing etc. After the material of the present invention has been coated on a matrix, it may optionally be cured at room temperature or elevated temperature.

The present invention also relates to a method of treating diseases with a laser-driven phototherapy, wherein the method can be performed only using the medical devices according to the present invention. Specifically, for example, the medical device obtained by the material of the present invention is placed on the desired region of a treatment. The medical device obtained by the material having a photosensitizer of the present invention can be brought into contact with the required region of the treatment (without an addition of a photosensitizer). By using a laser device, since the medical device of the present invention has a photosensitizer, on the one hand: based on the interaction between light, photosensitizer and oxygen, the photosensitizer absorbs photons so as to be in the excited state, and then the energy is passed to the surrounding oxygen so as to result in singlet-oxygen with a strong activity; the singlet oxygen, on the one hand, can cause an acute microvascular injury in diseased tissues, cause vascular blockages and cause ischemia, on the other hand, the singlet oxygen can directly kill diseased tissue cells, so as to achieve the purpose of local treatment. Moreover, on the other hand, since the medical device of the present invention has a photosensitizer, based on the photothermal conversion agent, the photothermal agent can efficiently convert light energy into heat energy and generate high temperature to kill diseased tissue cells under a radiation of laser with the selected wavelengths. When the temperature of the diseased tissue region reaches 43° C., such condition can inhibit DNA, RNA and protein synthesis.

It can be seen from the above that the material of the present invention and the medical device of the present invention completely do not use an exogenous photosensitizer (e.g. without pre-taking a photosensitizer etc.), and the process of the present invention does not need to add any additional agents (including additional photosensitizers). The present invention has the following advantages: non-invasive, non-toxic, highly efficient and the like.

The present invention also relates to the following technical solutions:

1. The matrix material can be molded into ophthalmic medical devices with safety, biocompatibility, functionality, which have good mechanical properties and can be sterilized.
2. The processing method of the matrix material according to item 1, including but not limited to: a turning method, a compression molding method, an injection molding method, a centrifugal casting method, a 3D printing method, and the like.
3. The sterilizing method of ophthalmic medical devices according to item 1, including but not limited to: moist heat sterilization, radiation sterilization, ethylene oxide sterilization and the like.
4. The distribution of photosensitizers in and on ophthalmic medical devices is, including but not limited to: overall uniform distribution, local distribution, zonal distribution, gradient distribution, scatter distribution etc.
5. The photosensitizer in ophthalmic medical device materials can be radiated again or repeatedly by laser with a selected wavelength, and each time the photosensitizer can be activated so as to generate activated oxygens or heats with high-temperature, so that the medical device can be repeatedly performed and always obtains efficacies.

EMBODIMENTS

Hereinafter, the present invention will be described in more detail with reference to the following Examples. However, these Examples are for the illustrative purpose only, and the invention is not intended to be limited by these Examples.

Example 1

Example 1a: Synthesis of Methyl Methacrylate-Photosensitizer Copolymer Materials In a beaker of 250 ml, 98.0 g methyl methacrylate monomer (MMA), 2.0 g ethylene glycol dimethacrylate (EGDMA), 0.12 g an initiator (azobisisobutyronitrile, AIBN), 0.04 g a photosensitizer (purpurin 18) were added therein, stirred uniformly, then transferred to a molding mould. After blowing nitrogen gas into the monomer solution, the mould was sealed, then placed in water bath with 65° C. for polymerizing for 24 hours, and then transferred to oven with 90° C. for 24 hours, obtained a material of polymethylmethacrylate comprising the photosensitizer purpurin 18. The molecular structure of purpurin 18 is as follows. Since the molecular structure of purpurin 18 comprises an ethylenically unsaturated double bond, which is capable of copolymerizing with MMA and EGDMA. Thereby, the porphyrin group (tetrapyrrole ring structure) having photoactivesis was fixed to the PMMA's molecular chain. In view of presence of EGDMA, PMMA molecular chains were crosslinked to obtain PMMA macromolecules having a network structure. The crosslinked polymer having a network structure can be swollen in a solvent, and cannot be dissolved. The photosensitizer (purpurin 18) molecules were firmly fixed into the PMMA material, and cannot freely enter into the blood or other body fluids.

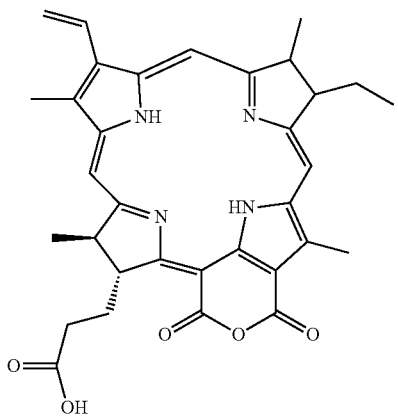 [SMILES: C=Cc1c(C)c2cc3nc(c4c5[nH]c(cc6nc(cc1[nH]2)C(C)C6CC)c(C)c5C(=O)OC4=O)[C@H](CCC(=O)O)[C@H]3C]

Purpurin 18

Example 1a-1x

The reaction conditions were substantially same as shown in Example 1a, wherein the differences were as follows:

| Monomer combination | photosensitizer |
|---|---|
| 1a MMA + EGDMA | Purpurin 18 |
| 1b EA + EMA + EGDMA | pheophorbide a |
| 1c MMA + BA + BDDMA | Chlorin e4 |
| 1d EA + EMA + TFEMA + EGDMA | Chlorin e6 |
| 1e PEA + PEMA + BDDMA | Chlorin p6 |
| 1f EA + St + EGDMA | Chlorin f |
| 1g EA + MSt + HDDMA | Methyl pheophorbide a |
| 1h POEA + BMA + EGDMA | Purpurin 18 methyl ester |
| 1i POEA + EMA + BDDMA | Chlorin e4 dimethyl ester |
| 1j POEA + BA + St + EGDMA | Chlorin e6 trimethyl ester |
| 1k EA + EOEMA + HDDMA | Chlorin p6 trimethyl ester |
| 1l EA + EMA + EOEOEMA + BDDMA | Chlorin f dimethyl ester |
| 1m POEA + EGDMA | Protoporphyrin |
| 1n St + DVB | Protoporphyrin dimethyl ester |
| 1o POEA + St + EGDMA | Pheophytin a |
| 1p HEMA + EGDMA | Protoporphyrin disodium |
| 1q HEMA + MMA + EGDMA | Fluorescein O-acrylate |
| 1r HEA + EGDMA | Purpurin 18 |
| 1s HEA + MMA + EGDMA | pheophorbide a |
| 1t HEMA + EA + EGDMA | Chlorin e4 |
| 1u HEMA + BA + EGDMA | Chlorin e6 |
| 1v HEMA + EA + POEA + EGDMA | Chlorin p6 |
| 1w HEA + BMA + EGDMA | Chlorin f |
| 1x HFIPMA + TMSPMA + TTMSBPMA + MAA + MMA + HEMA + EGDMA | Fluorescein O-methacrylate |

MMA: methyl methacrylate
EA: ethyl acrylate
EMA: ethyl methacrylate
BA: butyl acrylate
EGDMA: ethylene glycol dimethacrylate
BDDMA: butanediol dimethacrylate
HDDMA: hexanediol dimethacrylate
TFEMA: trifluoroethyl methacrylate
HEMA: hydroxyethyl methacrylate
HEA: hydroxyethyl acrylate
PEA: phenylethyl acrylate
PEMA: phenylethyl methacrylate
POEA: phenoxyethyl acrylate
BMA: benzyl methacrylate
EOEMA: ethoxyethyl methacrylate
EOEOEMA: ethoxyethoxy ethyl methacrylate
HFIPMA: hexafluoroisopropyl methacrylate
TMSPMA: methacryloxypropyl tris (trimethylsiloxy) silane
TTMSBPMA: 1,3-bis (methacryloxy propyl) tetra (trimethylsiloxy) disiloxane
MAA: methacrylic acid
St: styrene
MSt: methylstyrene
DVB: divinylbenzene.

Example 2

Example 2a: Synthesis of Silica Gel-Photosensitizer Copolymer Material

In a beaker of 250 ml, 0.04 g purpurin 18 (a photosensitizer) was added to silicone rubber two-component system (MED-6820, available from Nusil), stirred completely, and removed bubbles, then transferred to the molding mould. The mould was sealed, then placed in oven with 150° C. for polymerizing for 30 minutes, obtained a silica gel material comprising purpurin 18 photosensitizer agent. Since the molecular structure of purpurin 18 comprises an ethylenically unsaturated double bond, which is capable of copolymerizing with hydrogen-containing silicone oil and vinyl silicone oil. Thereby, the porphyrin group (tetrapyrrole ring structure) having photoactivesis was fixed to the molecular chain of silica gel. The photosensitizer (purpurin 18) molecules were firmly fixed into the silica gel material, and cannot freely enter into the blood or other body fluids.

Example 2a-2 q

The reaction conditions were substantially same as Example 2a, wherein the differences were as follows:

| Two-component silicone rubber's brand | photosensitizer |
|---|---|
| 2a MED-6820 | Purpurin 18 |
| 2b MED-6385 | pheophorbide a |
| 2c MED-6233 | Chlorin e4 |
| 2d MED-6219 | Chlorin e6 |
| 2e MED-6215 | Chlorin p6 |
| 2f MED-6210 | Chlorin f |
| 2g MED4-4420 | Methyl pheophorbide a |
| 2h MED2-4420 | Purpurin 18 methyl ester |
| 2i MED-4286 | Chlorin e4 dimethyl ester |
| 2j MED2-4244 | Chlorin e6 trimethyl ester |
| 2k MED-4211 | Chlorin p6 trimethyl ester |
| 2l MED-6820 | Chlorin f dimethyl ester |

-continued

| | Two-component silicone rubber's brand | photosensitizer |
|---|---|---|
| 2m | MED-6820 | Protoporphyrin |
| 2n | MED-6820 | Protoporphyrin dimethyl ester |
| 2o | MED-6820 | Pheophytin a |
| 2p | MED-6820 | Protoporphyrin disodium |
| 2q | MED-6820 | Fluorescein O-acrylate |

Example 3

Example 3a: Synthesis of Polypropylene-Photosensitizer Blend Materials

Accurately weighing 5 Kg polypropylene pellets (PP, R370Y, available from Korea SK) and 2 g purpurin 18 powder (a photosensitizer) were premixed. The pre-mixed raw materials PP/purpurin 18 were added in bis-screw extruder, blended, extruded and granulated, obtained the polypropylene material comprising a photosensitizer purpurin 18. Purpurin 18 was blended into polypropylene material. In view of a specific crystal structure of the polypropylene material, purpurin 18 molecules was firmly fixed to the polypropylene material, and cannot freely enter into the blood or other body fluids.

Example 3A-3o

The reaction conditions were substantially same as Example 3a, wherein the differences were as follows:

| | polymer | Photosensitizer |
|---|---|---|
| 3a | PP polypropylene | Purpurin 18 |
| 3b | HDPE High Density Polyethylene | Graphene |
| 3c | LDPE low density polyethylene | tungsten oxide $W_{18}O_{49}$ nanoparticles |
| 3d | TPU Thermoplastic Polyurethane | Copper sulfide $Cu_{7.2}S_4$ nanoparticles |
| 3e | PA Polyamide (PA, called: nylon) | Iron oxides of Fe @ $Fe_3O_4$ nanoparticles |
| 3f | PET polyethylene terephthalate | Nickel carbide of $Ni_3C$ nanoparticles |
| 3g | PEEK polyetheretherketone | molybdenum oxide $MoO_3$ nanoparticles |
| 3h | POM polyformaldehyde | Carbon Nanotubes |
| 3i | PC Polycarbonate | Gold nanoparticles |
| 3j | PS polystyrene | Gold nanoparticles |
| 3k | PVC polyvinyl chloride | Gold nanoparticles |
| 3l | ABS acrylonitrile - butadiene - styrene copolymer | Gold nanoparticles |
| 3m | PMMA polymethyl methacrylate | Gold nanoparticles |
| 3n | Polysulfone PSU | Gold nanoparticles |
| 3o | PTFE polytetrafluoroethylene | Gold nanoparticles |

PP: Polypropylene
HDPE: high density polyethylene
LDPE: low density polyethylene
TPU: Thermoplastic polyurethane
PA: Polyamide (nylon)
PET: polyethylene terephthalate
PEEK: polyether ether ketone
POM: POM
PC: Polycarbonate
PS: Polystyrene
PVC: polyvinyl chloride
ABS: acrylonitrile - butadiene - styrene copolymer
PMMA: polymethyl methacrylate
PSU: Polysulfone
PTFE: polytetrafluoroethylene The photosensitizers listed in the Examples have the following molecular structures:

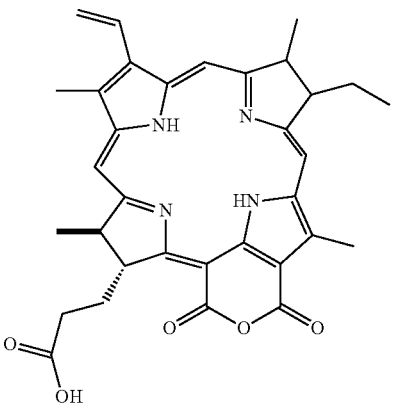

Purpurin 18

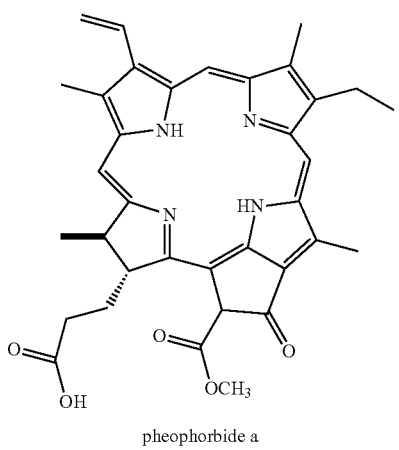

pheophorbide a

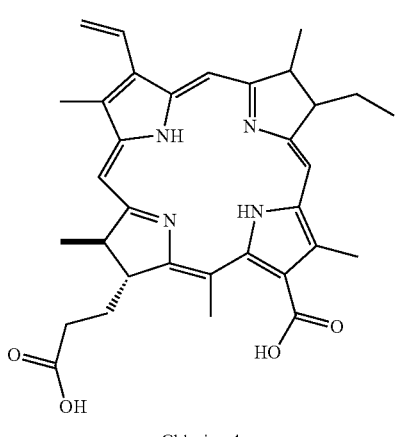

Chlorin e4

-continued
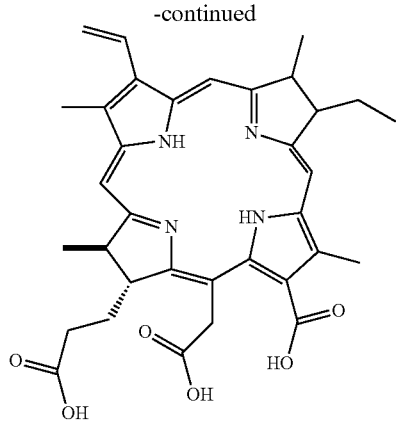
Chlorin e6
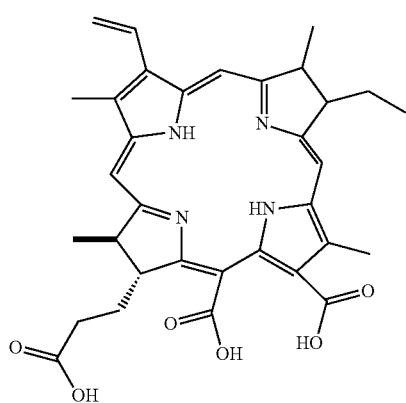
Chlorin p6
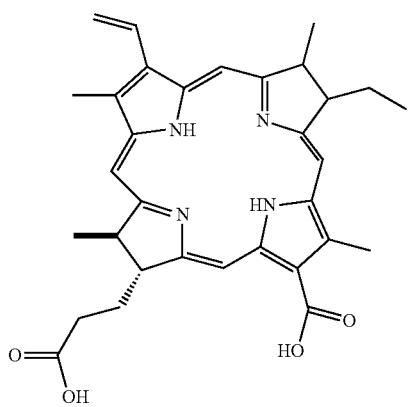
Chlorin f
-continued
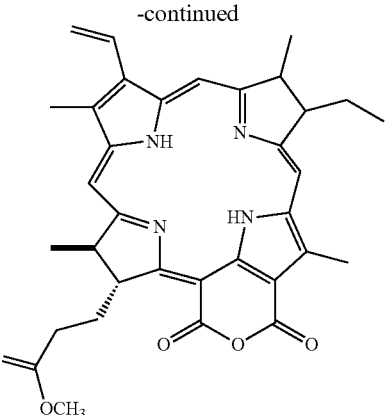
Purpurin 18 methyl ester
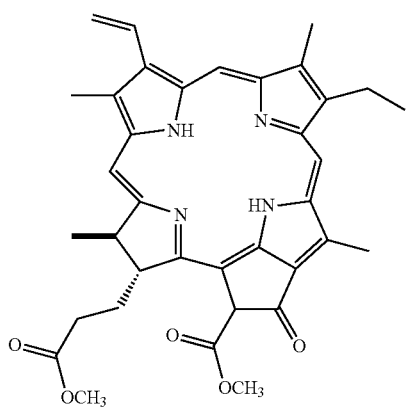
Methyl pheophorbide a
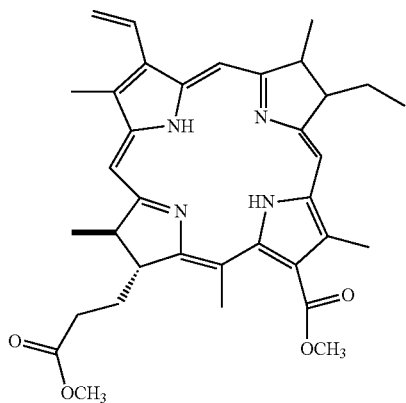
Chlorin e4 dimethyl ester

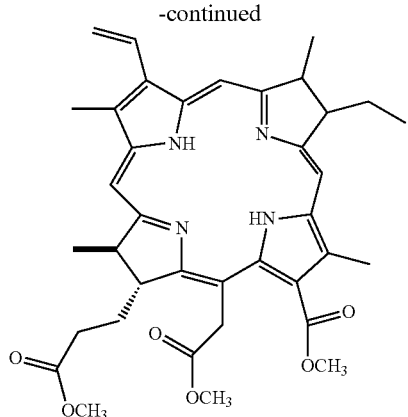
Chlorin e6 trimethyl ester
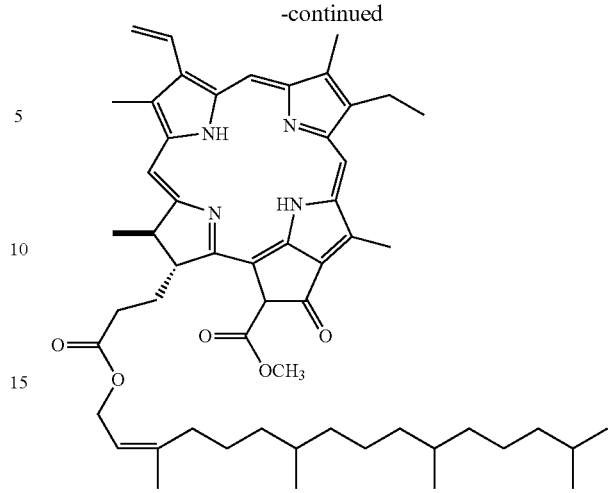
phaeophytin a
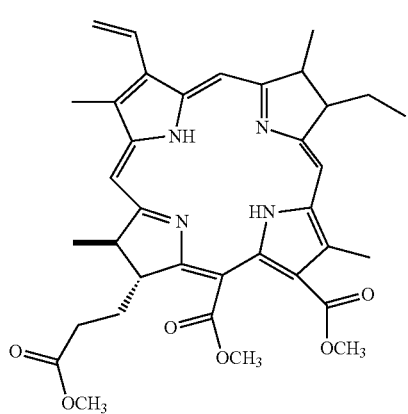
Chlorin p6 trimethyl ester
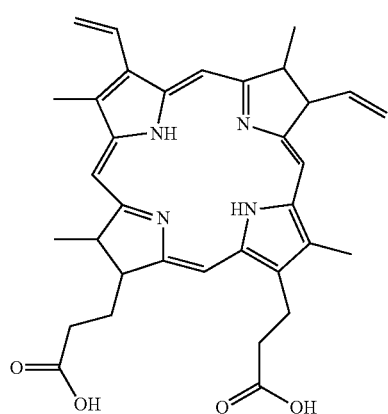
Protoporphyrin
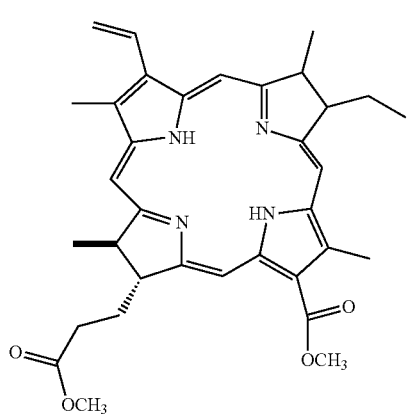
Chlorin f dimethyl ester
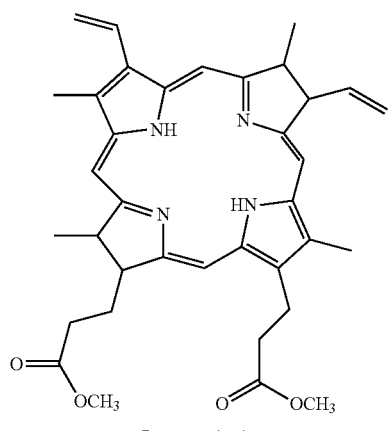
Protoporphyrin dimethyl ester

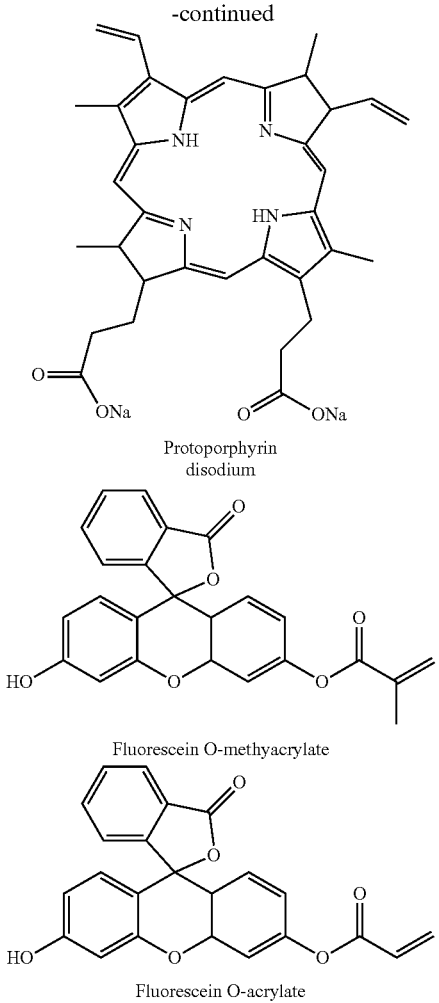

Protoporphyrin disodium

Fluorescein O-methyacrylate

Fluorescein O-acrylate

The above are only preferred embodiments of the present invention, which is not intended to limit the present invention. Clearly, those skilled in the art can make various modifications and variations to the present invention without departing from the spirit and scope of the present invention. Thus, if these modifications and variations of the present invention fall within the protection scopes of claims of the present invention and the protection scopes of equivalents thereof, the present invention intends to include these modifications and variations.

The invention claimed is:

1. An ophthalmic implant comprising an ophthalmic material for a light therapy of an ocular disease, comprising:
   a matrix material, in which the matrix material is a copolymer obtained by at least one monomer selected from the group consisting of methyl methacrylate, ethyl methacrylate, ethyl acrylate, butyl methacrylate, butyl acrylate, hydroxyethyl methacrylate, and hydroxyethyl acrylate and at least one monomer selected from the group consisting of ethylene glycol dimethacrylate, butanediol dimethacrylate and hexanediol dimethacrylate; and
   at least one photosensitizer selected from the group consisting of porphyrins, metalloporphyrins, porphins, chlorophyll or derivatives thereof,
   wherein the at least one photosensitizer is fixed inside the matrix material, and the photosensitizer is polymerized with the matrix material,
   wherein the amount of the at least one photosensitizer is less than 0.1 wt % relative to the total weight of the matrix material,
   wherein the at least one photosensitizer is a photothermal-type photosensitizer capable of generating heat such that, when subjected to a laser light source having a wavelength between 600 nm and 900 nm, the ophthalmic material experiences a temperature increase of about 6° C. to about 12° C., and
   wherein the ophthalmic material excludes a UV absorber.

2. The ophthalmic implant according to claim 1, wherein the photosensitizer is selected from the group consisting of chlorophyll derivatives, pheophytin, pheophorbide a, chlorine $e_6$, purpurins 18, chlorine p6, chlorine f, protoporphyrin, hematoporphyrin derivatives (HpD) and porfimer sodium.

3. A process for preparing the ophthalmic implant according to claim 1, comprising the following steps:
   1) Mixing a matrix material with a photosensitizer, as well as optional additives;
   2) molding the mixed raw materials;
   3) polymerizing the mixed raw materials such that the photosensitizer is polymerized with and fixed inside the matrix material.

4. The process according to claim 3, wherein the ophthalmic implant is molded by a process selected from the group consisting of extrusion, injection molding, blow molding, foaming, calendering, and spinning.

5. A medical device comprising the ophthalmic implant according to claim 1.

6. The medical device according to claim 5, wherein the medical device is selected from the group consisting of: intraocular lenses for preventing and/or treating a second cataract, corneal contact lens, iris hooks, artificial cornea, intracorneal ring, capsular tension ring, intracorneal lens, glaucoma drainage valve, intraocular fillers, and fundus fillers.

7. A method for preventing and/or treating a second cataract in a subject, comprising implanting the medical device according to claim 5.

* * * * *

UNITED STATES PATENT AND TRADEMARK OFFICE
CERTIFICATE OF CORRECTION

| | | |
|---|---|---|
| PATENT NO. | : 11,925,686 B2 | Page 1 of 1 |
| APPLICATION NO. | : 15/746746 | |
| DATED | : March 12, 2024 | |
| INVENTOR(S) | : Sui et al. | |

It is certified that error appears in the above-identified patent and that said Letters Patent is hereby corrected as shown below:

On the Title Page

(56) References Cited, OTHER PUBLICATIONS, Page 2, Column 2, Lines 20-21: Please correct "Japanese Application No. dated May 26, 2020." to read --Japanese Application No. 2018-503474 dated May 26, 2020.--

In the Specification

Column 8, Line 31: Please correct "550°" to read --55°--

In the Claims

Column 22, Line 32, Claim 3: Please correct "Mixing" to read --mixing--

Signed and Sealed this
Twenty-fifth Day of June, 2024

Katherine Kelly Vidal
*Director of the United States Patent and Trademark Office*